(12) United States Patent
Hooi

(10) Patent No.: US 10,945,891 B2
(45) Date of Patent: Mar. 16, 2021

(54) DRUG DELIVERY DEVICE

(71) Applicant: Calla Lily Personal Care Limited, London (GB)

(72) Inventor: (Alex) Yu Sing Hooi, London (GB)

(73) Assignee: Calla Lily Personal Care Limited, London (GB)

( * ) Notice: Subject to any disclaimer, the term of this patent is extended or adjusted under 35 U.S.C. 154(b) by 314 days.

(21) Appl. No.: 14/908,493

(22) PCT Filed: Aug. 1, 2014

(86) PCT No.: PCT/GB2014/052370
§ 371 (c)(1),
(2) Date: Jan. 28, 2016

(87) PCT Pub. No.: WO2015/015220
PCT Pub. Date: Feb. 5, 2015

(65) Prior Publication Data
US 2016/0184143 A1 Jun. 30, 2016

(30) Foreign Application Priority Data
Aug. 1, 2013 (GB) ..................... 1313784

(51) Int. Cl.
*A61F 13/20* (2006.01)
*A61M 31/00* (2006.01)
*A61F 13/84* (2006.01)

(52) U.S. Cl.
CPC ...... *A61F 13/2074* (2013.01); *A61F 13/2022* (2013.01); *A61F 13/8405* (2013.01); *A61M 31/00* (2013.01)

(58) Field of Classification Search
CPC .. A61F 13/2074; A61F 13/2022; A61F 13/26; A61F 2013/4729
See application file for complete search history.

(56) References Cited

U.S. PATENT DOCUMENTS

| | | | |
|---|---|---|---|
| 592,659 | A | 10/1897 | Miller et al. |
| 1,561,020 | A | 11/1925 | Pond |
| 2,092,346 | A | 9/1937 | Arone |
| 2,138,626 | A | 11/1938 | Irving |
| 2,331,355 | A | 10/1943 | Strongson |
| 2,670,736 | A | 3/1954 | Dunkelberger |
| 2,733,714 | A | 2/1956 | Haas |
| 3,037,506 | A | 6/1962 | Penksa |
| 3,058,469 | A | 10/1962 | Crockford |
| 3,420,234 | A | 1/1969 | Phelps |
| 3,674,029 | A | 7/1972 | Bates et al. |

(Continued)

FOREIGN PATENT DOCUMENTS

| | | |
|---|---|---|
| DE | 29611480 | 9/1996 |
| DE | 29620118 | 3/1998 |

(Continued)

*Primary Examiner* — Susan S Su
(74) *Attorney, Agent, or Firm* — Knobbe, Martens, Olson & Bear, LLP

(57) ABSTRACT

The present invention relates to a device for insertion into a human or animal cavity, the device comprising an internally wearable plug comprising a pharmaceutically active composition; an externally wearable anchor element; and a sheath joining the plug to the anchor element such 5 that a wearer's finger can be received in the sheath to assist insertion.

19 Claims, 7 Drawing Sheets

(56) References Cited

U.S. PATENT DOCUMENTS

| | | | |
|---|---|---|---|
| 3,690,321 A | | 9/1972 | Hirschman |
| 3,756,238 A | * | 9/1973 | Hanke ................ A61F 13/2051 |
| | | | 604/287 |
| 3,857,394 A | * | 12/1974 | Alemany ............ A61F 13/2051 |
| | | | 604/57 |
| 3,905,372 A | | 9/1975 | Denkinger |
| 3,946,737 A | | 3/1976 | Kobler |
| 4,237,888 A | * | 12/1980 | Roseman ............ A61F 13/2051 |
| | | | 424/430 |
| 4,286,596 A | | 9/1981 | Rubinstein |
| 4,503,098 A | * | 3/1985 | Potts ................. A61F 13/15252 |
| | | | 427/394 |
| 4,627,848 A | | 12/1986 | Lassen et al. |
| 5,113,873 A | | 5/1992 | Boarman |
| 5,180,059 A | | 1/1993 | Shimatani et al. |
| 5,193,684 A | | 3/1993 | McDonald |
| 5,290,262 A | | 3/1994 | Vukos et al. |
| 5,361,779 A | | 11/1994 | Wilson, III |
| 5,383,868 A | | 1/1995 | Hyun |
| 5,389,181 A | | 2/1995 | Vukos et al. |
| 5,690,625 A | | 11/1997 | Widlund |
| 5,827,256 A | | 10/1998 | Balzar |
| 5,891,123 A | | 4/1999 | Balzar |
| 5,964,741 A | | 10/1999 | Moder |
| 6,059,763 A | | 5/2000 | Brown |
| 6,348,047 B1 | | 2/2002 | Harper |
| 6,416,779 B1 | * | 7/2002 | D'Augustine ............ A61F 6/08 |
| | | | 424/430 |
| 6,840,927 B2 | | 1/2005 | Hasse |
| 6,863,664 B2 | | 3/2005 | Wada |
| 6,939,333 B1 | | 9/2005 | Franklin, Jr. |
| 7,112,192 B2 | | 9/2006 | Hasse |
| 8,672,872 B2 | | 3/2014 | Hooi |
| 9,265,668 B2 | | 2/2016 | Hooi |
| 2003/0045829 A1 | * | 3/2003 | Gehling .............. A61F 13/2051 |
| | | | 604/11 |
| 2003/0120224 A1 | * | 6/2003 | Geiser ................ A61F 13/2051 |
| | | | 604/285 |
| 2003/0153864 A1 | * | 8/2003 | Chaffringeon ...... A61M 31/002 |
| | | | 604/15 |
| 2003/0187416 A1 | | 10/2003 | Shimoe |
| 2004/0024376 A1 | | 2/2004 | Ohba |
| 2004/0043071 A1 | * | 3/2004 | Pauletti ................ A61K 9/0034 |
| | | | 424/484 |
| 2004/0147893 A1 | | 7/2004 | Mizutani et al. |
| 2004/0147897 A1 | | 7/2004 | Mizutani et al. |
| 2004/0225272 A1 | | 11/2004 | Karapasha |
| 2005/0055003 A1 | | 3/2005 | Bittner |
| 2007/0128254 A1 | * | 6/2007 | Heuer .................. A61K 9/0036 |
| | | | 424/443 |
| 2008/0077105 A1 | | 3/2008 | Hooi |
| 2009/0131852 A1 | | 5/2009 | Hooi |
| 2012/0089111 A1 | * | 4/2012 | Magnusson ........ A61F 13/2051 |
| | | | 604/385.18 |
| 2012/0197230 A1 | | 8/2012 | Hooi |

FOREIGN PATENT DOCUMENTS

| | | |
|---|---|---|
| EP | 0 104 039 A1 | 3/1984 |
| EP | 136524 A1 | 4/1985 |
| EP | 1 206 925 A2 | 5/2002 |
| EP | 2 201 918 A2 | 6/2010 |
| FR | 2590161 | 11/1985 |
| FR | 2 653 328 | 10/1989 |
| JP | 08-112311 A | 5/1996 |
| JP | 2000-237234 | 9/2000 |
| JP | 2003-010243 | 1/2003 |
| JP | 2005-177074 A | 7/2005 |
| WO | WO 94/22405 | 10/1994 |
| WO | WO 02/058611 A1 | 8/2002 |
| WO | WO 03/015676 A2 | 2/2003 |

\* cited by examiner

DRUG DELIVERY DEVICE

CROSS-REFERENCE TO RELATED APPLICATIONS

This application is the U.S. National Phase under 35 U.S.C. § 371 of International Application No. PCT/GB2014/052370, filed Aug. 1, 2014, which claims priority to Great Britain Application No. 1313784.9, filed Aug. 1, 2013.

The present invention relates to a drug delivery device, more particularly to a device for vaginal and/or rectal drug delivery.

The delivery of drugs through the vaginal or rectal cavity is known to be advantageous in that both local and systemic administration of the drug can be achieved and provides an alternative to the traditional delivery routes. In some instances, oral delivery is not recommended because of gastro-intestinal side effects or decrease in bioavailability or simply because the patient is uncooperative or cannot swallow the medication. Parenteral drugs (e.g. intravenous injections) might not be suitable, as they must usually be administered by trained practitioners.

Vaginal and rectal drugs (such as creams and pessaries) can be applied with a gloved finger. However, with creams, when the finger is inserted into the vagina or rectum, a portion of the drug that will be retained by the vaginal and rectal walls, will not be applied to the targeted area. It is therefore difficult to administer an accurate amount of drug to the targeted area. In addition, this method is not suitable when the targeted area is located deeper than the length of the inserted portion of the finger.

Drugs can be delivered by inserting suppositories or by injecting the drugs via a syringe or a spray. However, due to their physical function, both vaginal and rectal cavities have a tendency to reject foreign bodies and although the drugs might reach the targeted area but are not retained within the cavity and adequate amount of the drug cannot be achieved. Elastomeric vaginal rings have been developed to retain the leaking drug, but these devices are uncomfortable for the wearer.

A number of medicated tampons and sponges are known for delivery of drugs to the vaginal or rectal cavity. These devices are usually inserted using an applicator or inserter, which is uncomfortable and it is often difficult to properly position the tampon.

This is particularly so in the case of vaginal drug delivery, in which the medicated tampon must be positioned behind the cervix. If the tampon is not inserted deep enough then there is a risk that the drug will not reach the target area and that it is rejected by the vagina. Standard applicators and inserters are usually too short to achieve correct positioning, or when they are of sufficient length, the user might not push the tampon deep enough by fear of injury or pain. It is recommended that the medicated tampon is inserted by an experienced practitioner so for accurate positioning. However, this is not, in practice, possible since most tampon-wearing women experience discomfort after urinating (because they feel that the tampon and/or cord is soiled) and replace the tampon after each visit to the bathroom. Even an experienced practitioner will have difficulty in inserting a medicated tampon using an applicator because of the absence of sensitivity and to help with the insertion procedure the patient will need to lie down.

In the case of rectal drug delivery, in which the targeted area is in the rectum above the sphincter, applicators are not recommended because of the tightness of the sphincter. This is particularly the case where the patient will have a tendency to clench his/her sphincter during the insertion procedure thereby increasing the risk of injury to the mucosa.

It is an object of this invention to mitigate problems such as those described above.

According to a first aspect of the invention, there is provided a device for insertion into a human or animal cavity, the device comprising an internally wearable plug comprising a pharmaceutically active composition; an externally wearable anchor element; and a sheath joining the plug to the anchor element such that a wearer's finger can be received in the sheath to assist insertion.

In the context of this invention, the expressions "internally worn" and "internally wearable" mean inside the cavity and "externally worn" and "externally wearable" mean outside the cavity.

The invention seeks to provide a device for the delivery of a drug into a cavity, so that an accurate amount of drug is administered to the targeted area. The device according to the present invention is easy to use and therefore the device can be correctly positioned by the wearer himself/herself and the drug can be self-administered.

The human cavity is preferably a vaginal cavity or a rectal cavity. The target areas are often behind the cervix for vaginal drug administration and past the sphincter for rectal drug administration. As explained above, these areas are often difficult to reach, but the device of the present invention enables easy application and accurate positioning, without the involvement of a medical practitioner.

The pharmaceutically active composition may comprise or consist of a topically active composition. This method of delivery is particularly advantageous to efficiently treat local conditions in situ in the cavity. With other delivery routes, part of the initially administrated amount of drug is likely to be lost while travelling to the area to be treated so an inaccurate or insufficient amount of drug is administered to the affected area.

The pharmaceutically active composition may comprise or consist of a systemically active composition. This method of delivery is particularly advantageous when other administration routes are not suitable, for example, when a patient is not capable (when unconscious, vomiting or convulsing), has a phobia against or unwilling to taking tablets, pills or capsules or when no parenteral preparation of the drug is available.

Preferably, the composition comprises one or more pharmaceutically active ingredients selected from an antifungal agent, an antibacterial and/or hormonal preparations for vaginal delivery, antibacterial, analgesics and/or antiepileptic agent, medication for hemorrhoids for rectal delivery. The composition may be that of a solution, a lotion, a cream, an emulsion, a suspension, an ointment, a paste, a gel, a powder and/or foam.

In a preferred embodiment, the composition is releasable in the presence of heat and/or fluid. In this embodiment, the composition remains on and/or in the plug when not in use. When the plug is inserted into the cavity, the composition can be released and/or activated due the body temperature of the wearer and/or in the presence of body fluids.

Preferably, the plug comprises or consists of an absorbent material. The pharmaceutically active composition is released into the cavity and mixes with the wearer's body fluids. The absorbent plug can recover any excess fluid, while ensuring the target area remains in contact with the pharmaceutically active composition for prolonged periods. Excess fluid can potentially mix with the composition and be rejected by the cavity and should therefore be removed to ensure that an accurate amount of drug is delivered to the target area. For example, the plug may be a solid cylinder, for example of compressed cotton or tampon-like product and may comprise a wad of absorbent material.

The plug may be saturated with the pharmaceutically active composition. Once positioned in the cavity, the composition will be released from the plug and spread to the area adjacent the plug. The composition can then treat the areas in contact with the plug and/or diffuse into systemic circulation.

In a preferred embodiment, the plug comprises a heat labile membrane or a liquid labile membrane. In the context of the invention, the expression "heat labile" or "liquid labile" generally means "which undergoes a change when heated or in the presence of liquid", respectively. The membrane may undergo chemical and/or physical change when heated (for example by the body heat in the cavity) or in the presence of liquid (for example body fluids).

The change can for example be dissolution or disintegration, the membrane can act as a plug protector so that, when not in use, the medicated plug is not contaminated and loss of composition is prevented. When the device is in use and the plug inserted, the membrane dissolves and the composition can be released from the plug. The membrane is preferably made of a biocompatible material to avoid any potential infection.

In another preferred embodiment, the membrane itself comprises the pharmaceutically active composition so that, in use, the membrane dissolves inside the cavity thereby releasing the pharmaceutically active composition.

The device may further comprise a plug cover to protect the plug from contamination and to prevent any loss of composition from the plug. Preferably, the plug cover comprises a liquid impermeable layer. The plug cover is preferably removable or detachable from the plug before insertion of the plug into the cavity.

In a preferred embodiment of the invention, the anchor element is an externally wearable absorbent anchor element, such as an absorbent pad. One function of the anchor element is to prevent the inserted plug from moving within the cavity. Once the plug is inserted in the correct position, the plug can moved downwards in the cavity but it can also move upwards. This is a worry for the wearer because, without the anchor element, the plug could move deeper into the cavity and be difficult, if not impossible, to remove without professional assistance. The anchor prevents the plug from moving deeper into the cavity.

Another important function of the anchor element is to recover any fluid rejected by the cavity. Preferably, the anchor element comprises an absorbent layer. Because of the nature and functions of the vaginal and rectal cavities, body fluids (and also some composition mixed with the body fluids) can be rejected by the cavity and soil the wearer's clothes. Preferably, the anchor element comprises a liquid impermeable layer, such as a liquid impermeable backing sheet so that any fluid rejected by the cavity and/or absorbed by the absorbent layer does not soil the wearer's clothes.

The absorbent pad may further comprise an adhesive sheet to secure the pad to the wearer's underwear or other clothing. Most preferably, the anchor element is an externally wearable pad comprising an absorbent layer facing the cavity in use, and an impermeable layer facing the underwear.

In a preferred embodiment of the invention, the sheath is flexible. This allows the wearer's finger to easily move the plug inside the cavity and to correctly position the plug adjacent the targeted area. It is also preferred that the sheath terminates at the plug, i.e. at the end of the plug nearest the cavity opening in use, so that the finger can reach the plug and directly manipulate it. A flexible sheath also minimises the risk of injury and discomfort that might occur when the plug is inserted using a rigid applicator.

The sheath should be able to receive a finger, which is likely to have roughly the same or a slightly larger diameter than a small conventional tampon. Therefore, the sheath is preferably expandable in a radial direction. Preferably, the sheath is not significantly expandable in the longitudinal direction as this can lead to the plug being misplaced. Most preferably, the length of the sheath is such that, when the sheath is fully extended in use, the plug is located adjacent the targeted area in the cavity. In other words, the length of the sheath is substantially equal to the distance between the cavity opening and the area to be treated.

Preferably, the sheath comprises an impermeable layer or a tube of impermeable material so that bodily or other fluids do not enter the inside of the sheath and the finger is protected. Preferably, the impermeable layer or impermeable material is closed at the end of the sheath that joins the plug to prevent the finger becoming soiled by fluids in the plug (e.g. pharmaceutically active composition and/or bodily fluids).

Preferably, the sheath comprises an absorbent layer or a tube of absorbent material. The absorbent material may be such that the absorbed fluids travel from the plug to the anchor element or absorbent pad thereby maximising the absorptive capacity of the device. Alternatively, the absorbent material may be such that the absorbed fluids remain at the absorption site. Thus, when the pharmaceutically active composition is mixed with the fluids and retained by the absorbent material of the sheath, maximum exposure of the drug to the targeted area can be achieved. Preferably, the sheath comprises an internal impermeable layer and an external absorbent layer. For example, the sheath may comprise an internal tube of impermeable material and an external tube of absorbent material.

In a preferred embodiment, the device further comprises a cord attached to the plug to assist removal of the plug from the cavity. Preferably, the cord extends inside the sheath.

In a second aspect of the invention, there is provided a method of using a device as described above, the method comprising the step of inserting a finger into the sheath and pushing the plug into the cavity.

In a third aspect of the invention, there is provided a method for the delivery of a pharmaceutically active composition into a human or animal cavity, the method comprising the use of a device as described above.

In a fourth aspect of the invention, there is provided a method for the treatment of a vaginal or rectal condition, the method comprising the use of a device as described above.

In a fifth aspect of the invention, there is provided a method for manufacturing a device as described above, the method comprising the step of joining an internally wearable plug comprising a pharmaceutically active composition to an externally wearable anchor by a sheath.

The invention will be further described with reference to the drawings and figures, in which FIG. 1 is a side view of a device according to the present invention, in which the pad is folded outwardly;

Figure 1:
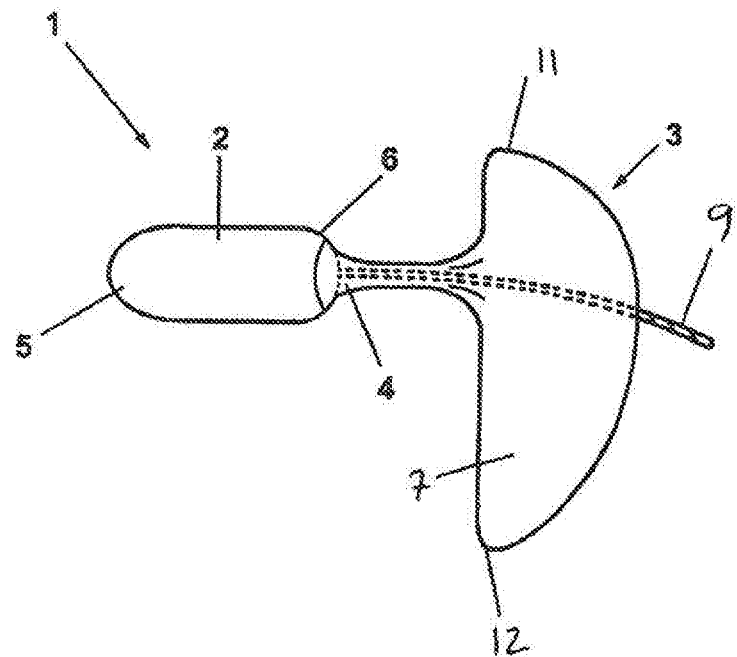
Figure 2:
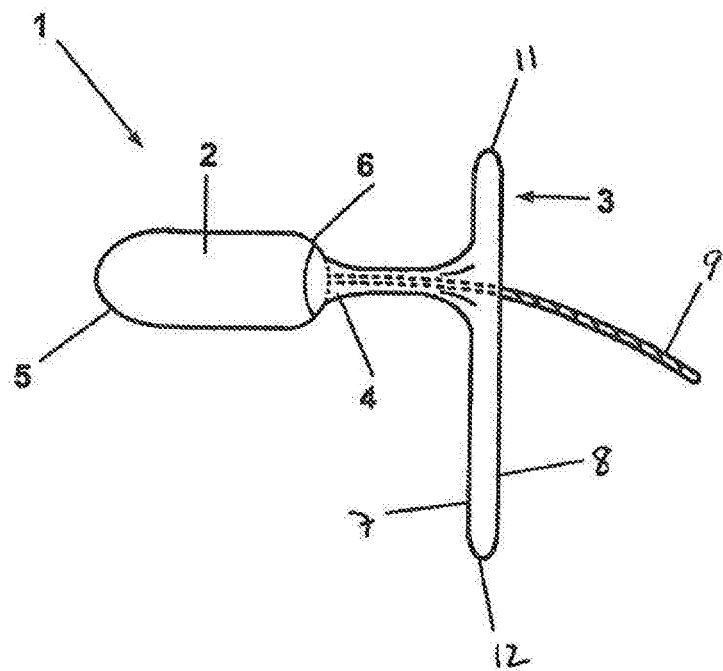
FIG. 2 is a side view of the device of FIG. 1, in which the pad is flat.

Referring to FIG. 1, there is illustrated a device 1 for insertion into a human or animal cavity, the device 1 comprising an internally wearable plug 2 comprising a pharmaceutically active composition; an externally wearable anchor element 3; and a sheath 4 joining the plug 2 to the anchor element 3 such that a wearer's finger can be received in the sheath 4 to assist insertion.

The plug 2 is substantially cylindrical so that it fits comfortably in a vaginal or rectal cavity. The end of the plug 2 that, in use, is inserted into the vaginal cavity first is referred to as the innermost end 5 of the plug 2. The end of the plug 2 that, in use, is inserted into the vaginal cavity last is referred to as the outermost end 6 of the plug 2. Both the innermost end 5 and outermost end 6 of the plug 2 are domed to ease insertion and removal of the plug 2 from the cavity.

The plug 2 is made from compressed cotton. For example, a sheet of compressed cotton may be cut and rolled into an appropriate shape. Other suitable materials and constructions may be used as desired.

The plug 2 comprises a pharmaceutically active composition. The composition can act locally as a topical composition and/or can diffuse through the cavity wall and have a systemic effect. If body fluids are present that might flush the composition out of the cavity, the absorbent material of the plug 2 can retain the fluid-composition mixture, thereby increasing the contact (and therefore administration) time.

The composition can be present in the plug 2 in several ways. For example, the plug 2 can be saturated with the composition so that it is slowly released to the vaginal or rectal tissue when positioned in the cavity.

Figure 9:
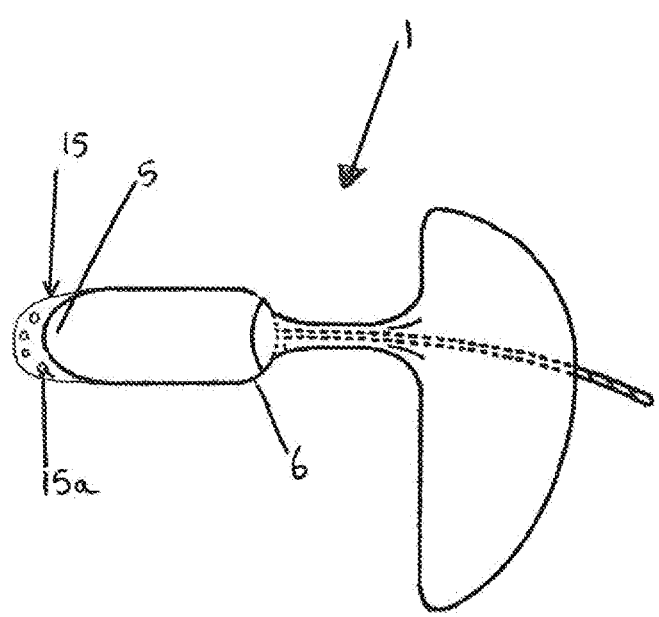
FIG. 9 is a side view of a device according to the present invention comprising a distal perforated drug reservoir.
Figure 10:
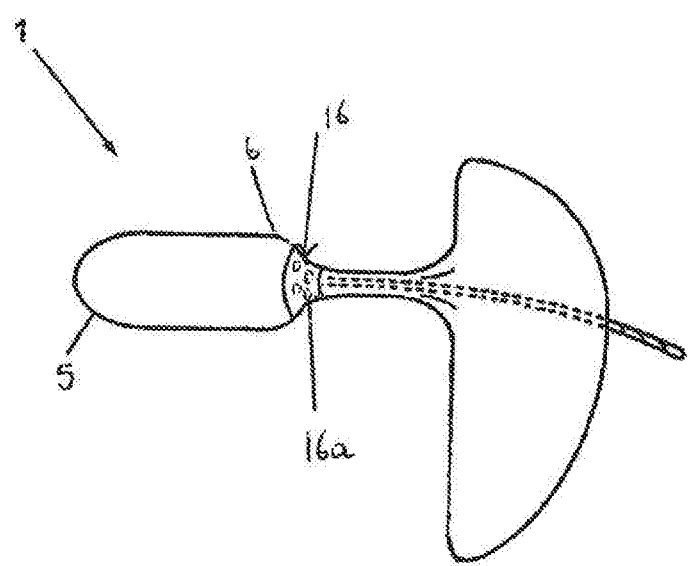
FIG. 10 is a side view of a device according to the present invention comprising a proximal perforated drug reservoir.

The composition can also be present at either or both ends of the plug 2. For example, there may be a drug reservoir at the innermost end 5 of the plug 2 or at the outermost end 6. In a preferred embodiment, there may be a drug reservoir 15 at the innermost end 5 of the plug 2, shown with perforations 15a in FIG. 9; or a drug reservoir 16 at the outermost end 6 of the plug 2 (or the innermost end of the sheath 4), shown with perforations 16a in FIG. 9. When the drug reservoir 16 is located at the outermost end 6 of the plug 2, the sheath 4 (or its impermeable layer) may be closed where it joins the reservoir 16, and the reservoir 16 may be configured to release the drug upon insertion, i.e. upon application of pressure with the finger. For example, the perforations 16a could be made of a material such that they burst open upon application of pressure.

The plug 2 can comprise a membrane which retains the composition, when the device 1 is not in use, and releases it when the plug 2 is positioned in the cavity.

In a first example, the membrane 14 can be perforated so that the composition is released through the openings 14a from a medicated plug 2.

In a second example, the membrane can be labile (e.g. dissolved or disintegrate) in the presence of a liquid, such as body fluids, and/or when heated, for instance, at the cavity (body) temperature of the wearer so that the composition is released from a medicated plug 2.

In a third example, the membrane itself may comprise the composition and release it when the plug 2 is positioned in the cavity. In this example, the medicated membrane can be heat or liquid labile as explained above.

Heat labile membranes may be used for both vaginal and rectal drug delivery. Liquid labile membranes can also be used in both applications, but are preferred for use in vaginal drug devices, since there are more body fluids present in the vaginal cavity than the rectal cavity. The labile membranes may be perforated or not perforated.

The device 1 may comprise a plug cover 13 in order to prevent contamination of the device 1. In addition, the cover 13 can prevent the loss or alteration of the composition before use.

Thus, the device 1 of the present invention enables the delivery of a pharmaceutically active composition. In particular, with the device 1 of the present invention, an extended contact (and therefore administration) time can be achieved. In the case of the vaginal or rectal administration of a drug using a syringe or conventional suppository, the drug is released at one go and is likely to be promptly rejected by the cavity, especially if the patient is in a standing or sitting position. In addition, the present invention allows the slow release of a drug without the need for complex pharmaceutical formulation (e.g. micro-encapsulated drugs) and is versatile in that it can be used in combination with a large variety of pharmaceutical compounds.

The amount of drug delivered can be easily controlled. A substantial amount of the drug is retained adjacent the plug 2 and there is therefore no need to "overload" the device 1 to compensate for losses due to natural rejection from the cavity.

The concentration and amount of drug may be adjusted depending on the drug(s) to be administered, the components of the composition, the form of the composition (e.g. solution, a lotion, a cream, an emulsion, a suspension, an ointment, a paste, a gel, a powder and/or a foam), the condition to be treated and the like. Another factor that may be taken into consideration is that the wearer will tend to replace the device 1 after bowel movement and/or urination. Thus, the amount of drug in each device 1 can be adjusted in consequence, and for example, devices 1 for use in the daytime may comprise less composition, than devices 1 for use in the night when the device is worn for a longer period of time.

The sheath 4 is tubular and extends from the outward end 6 of the plug 2 to the pad 3. More specifically, the sheath 4 comprises a tube of absorbent material with a layer of liquid impermeable material on its inside surface. In other words, there is a tube of liquid impermeable material inside the tube of absorbent material. The tube of absorbent material extends to the inward surface 7 of the pad 3. Indeed, the absorbent material of the sheath 4 can be integral with the absorbent layer of the pad 3. The tube of liquid impermeable material extends through the pad 3 to the outward surface 8 of the pad 3. Indeed, the tube of liquid impermeable material can be integral with the liquid impermeable backing of the pad 3.

The tube of liquid impermeable material and hence the sheath 4 is open on the outward surface 8 of the pad 3. An opening 10 formed by the sheath 6 on the outward surface 8 of the pad 3 can be seen in FIG. 4. In this embodiment, the tube of liquid impermeable material is closed where it joins the plug 2. This prevents liquid absorbed by the plug 2 passing into the inside of the sheath 4 and soiling the inserting finger.

A small diameter is required to improve the comfort of the device 1 in the region of the cavity orifice and the diameter of the sheath 4 is preferably smaller than that of the plug 2. However, the diameter must be sufficient to allow a finger to be accommodated inside the sheath 4. The sheath 4 is therefore expandable in a radial direction. This is accomplished by the sheath 4 being elastic in the radial direction so that the unexpanded diameter of the sheath 4 is smaller than that of the plug and the expanded diameter is sufficient to accommodate a finger. In one embodiment, an elastic tube (not shown) is provided between the absorbent tube and the liquid impermeable tube of the sheath 4. In other embodiments, either or both of the absorbent and liquid impermeable tubes of the sheath 4 are themselves elastic.

As explained above, the plug 2 can be easily guided and positioned within the cavity due to the insertion procedure. In order to further assist the positioning, the length of the sheath 4 can be chosen so that the plug 2 is inserted not too close to the cavity orifice and not too deep into the cavity. Furthermore, the sheath 4 can be substantially not expandable in the longitudinal direction in order to prevent movement of the plug 2 within the cavity.

The pad 3 is substantially circular, oval, rectangular or any other suitable shape. The pad 3 can be a standard rectangular napkin or a small interlabial pad. In a preferred embodiment as shown in the figures, the pad 3 is a flat-egg shaped that has a smaller back portion 11 and a larger front portion 12 when used as a vaginal device, and a larger back portion 11 and a smaller front portion 12 when used as a rectal device. Of course, the shape could be the same for either vaginal or rectal use, with the wearer suitably positioning the shorter and longer portions.

Figure 3:
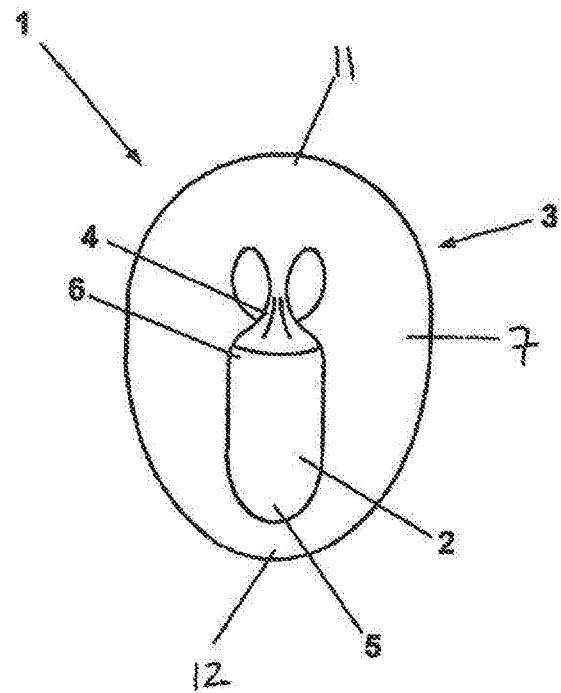
FIG. 3 is a front view of the device of FIG. 1.
Figure 4:
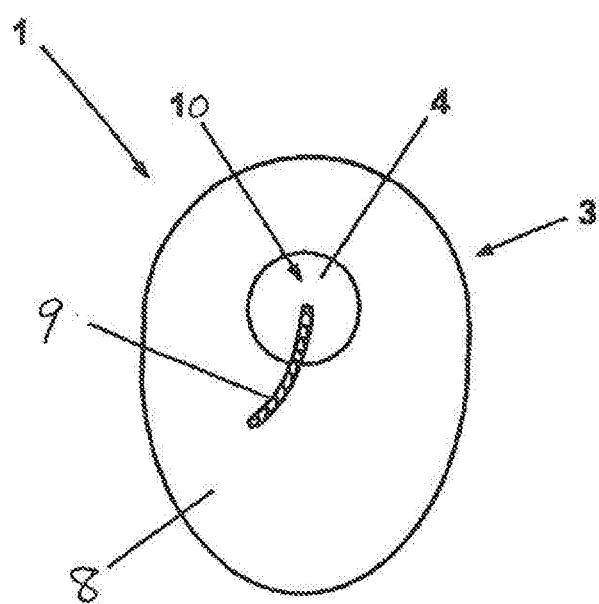
FIG. 4 is a rear view of the device of FIG. 1.

The side of the pad 3 in contact with the cavity in use is referred to as the inward side 7 (shown as the front of the device 1 in FIG. 3) and the side of the pad 3 in contact with clothing in use is referred to as the outward side 8 (shown as the rear of the device 1 in FIG. 4).

The pad 3 has an absorbent layer on the inward side 7 and a liquid impermeable layer on the outward side 8. In this embodiment, the absorbent layer is made from compressed cotton and the liquid impermeable layer is made from a polymeric material. Other suitable materials may be used as desired.

A cord 9 is provided to aid removal of the device. In this embodiment, the cord 9 extends inside the sheath 4 from the outward end of the plug 2 and out through the opening 10. When the wearer pulls on the cord 9 to remove the plug 2, the plug 2 is pulled outwardly from the cavity. The pad 3 tends to begin to fold around the plug 2 and the sheath 4 can invert to accommodate the plug 2. Thus, the cord 9 can be used to pull the plug 2 into the sheath 4, which can turn inside out to accommodate the plug 2. The wearer therefore retrieves the plug 2 inside the sheath 4 and with the pad 3 folded around the plug 2 and sheath 4 combination. There is therefore a very low chance of the wearer touching a soiled part of the device.

The term cord is not intended to be limiting to any particular type of twine or thread. Rather, it is a general term referring to any usable string or tail which the wearer can pull to extract the plug.

In use, the device 1 is removed from its packaging and one of the wearer's finger is inserted in the sheath 4 through the opening 12 to the outward end 6 of the plug 2. The elasticity of the sheath 4 allows it to expand radially and accommodate the finger. The protective cover 13 is removed from the plug 2. Thus, the user does not need to directly touch the plug 2 with his/her hands during the insertion procedure.

The wearer orients the device 1 so that the plug 2 extends longitudinally toward the vaginal or rectal cavity. The smaller back portion 11 of the pad 3 is positioned approximately at the rear of the vagina, i.e. toward the anus, and the larger front portion 12 of the pad 3 is positioned approximately at the front of the vagina, i.e. toward the pubic bone, when the device is used for vaginal delivery. When the device is used for rectal delivery, the pad 3 is positioned in the opposite direction.

The plug 2 is aligned with the orifice and inserted through the orifice and into the cavity. The plug 2 is pushed into the cavity until the inward surface 7 of the pad 3 comes to rest against the surface of the vagina or, more specifically, the vulva, between the labia majora. The finger is then withdrawn from the sheath 4, leaving the device 1 in place.

The composition is released from the device 1 into the cavity and more particularly in the area adjacent the plug 2.

If the device 1 comprises a perforated membrane, then the composition is released from the plug 2 through the openings. If the device 1 comprises a labile membrane, then the membrane dissolves or disintegrate, to release the composition from the plug 2. If the labile membrane comprises the pharmaceutically active composition, then the membrane dissolves or disintegrate to release the composition from the membrane.

Once released, the composition will contact the cavity walls and treat the condition locally in the case of a topical drug composition, or will diffuse through the walls, in the case of a systemic drug composition.

The absorbent plug 2 can recover any surrounding body fluids, which in excess might drag the composition out of the cavity. A further advantage is that any drug mixed with body fluid can also be recovered and retained adjacent the plug 2 from prolonged contact and administration. Excess body fluid can also be drawn along the absorbent layer of the sheath 4 and absorbed by the pad 3.

Figure 5:
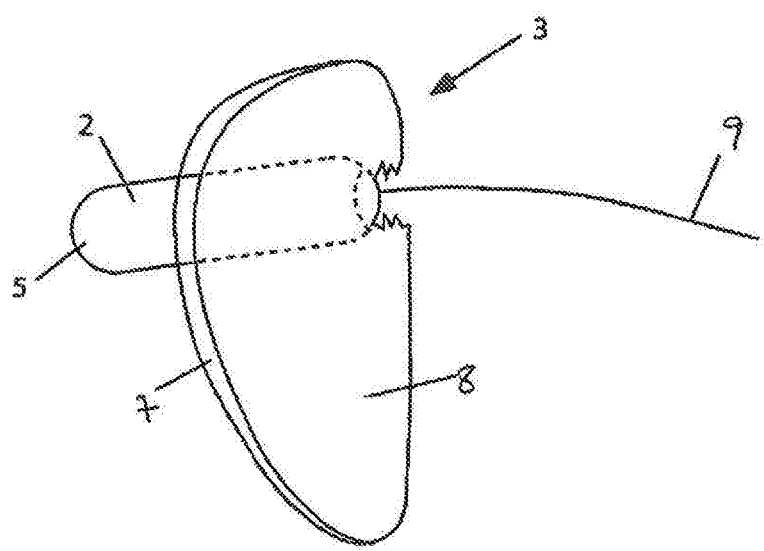
FIG. 5 is a side view of the device of FIG. 1, after use and during removal of the plug.

To remove the device 1, the wearer can grasp the cord 9 and pull it to remove the plug 2 from the cavity. As the plug 2 is pulled out of the cavity, the pad 3 can be folded, as shown in FIG. 5. The outward surface 11 of the pad 3 is pushed or grasped by the wearer to fold the pad 3 over the plug 2 and sheath 4 and the inward surface 7 effectively becomes enclosed by the outward surface 8. This folding of the pad 3 can reduce the likelihood of the wearer touching the soiled inner surface 7 of the pad 3. As this inward surface 7 is typically soiled during use and the outward surface 8 is generally relatively clean, hygiene can therefore be maintained.

Furthermore, as the internally worn plug 2 is removed from the cavity, it can be accommodated by the folded pad 3. The grasping of the pad 3 as the plug 2 is pulled out of the cavity can cause the pad 3 to fold over the plug 2. Indeed, the plug 2 can be enclosed by the pad 3. Again, as the plug 2 is generally soiled, but the surface 8 of the pad 3 grasped by the wearer is generally relatively clean, the likelihood of the wearer touching the plug 2 during removal of the device is reduced and hygiene is maintained.

Figure 6:
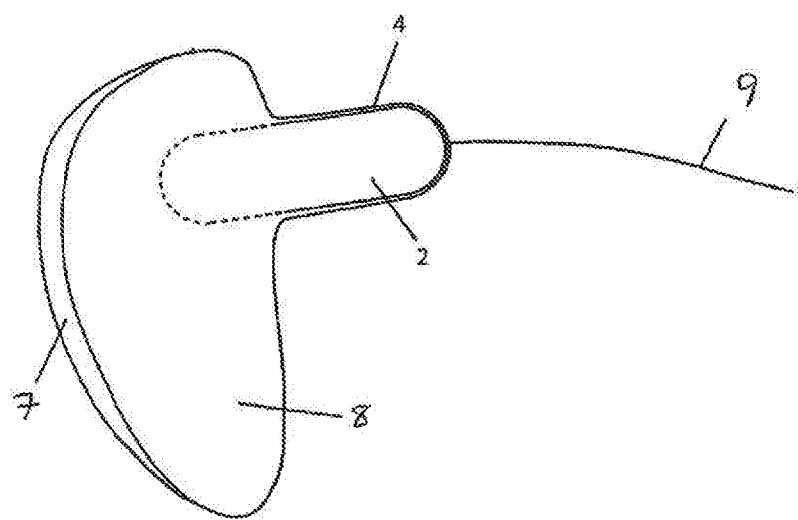
FIG. 6 is a side view of the device of FIG. 1, after use and after removal of the plug.
Figure 7:
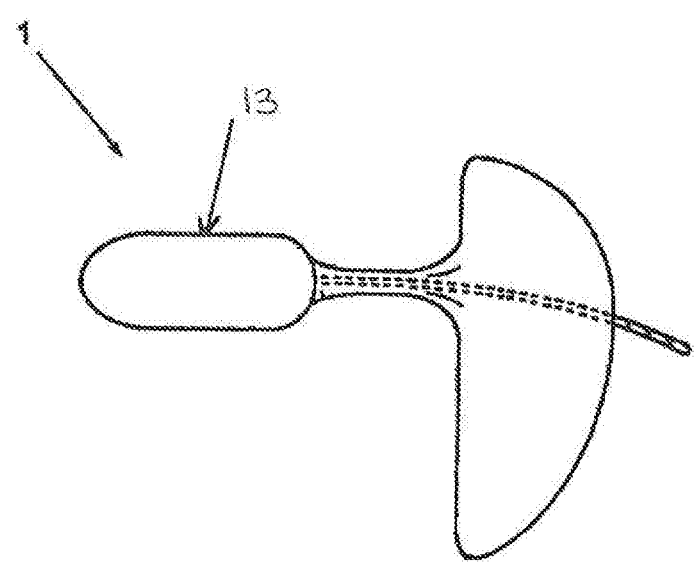
FIG. 7 is a side view of a device according to the present invention comprising a plug cover.
Figure 8:
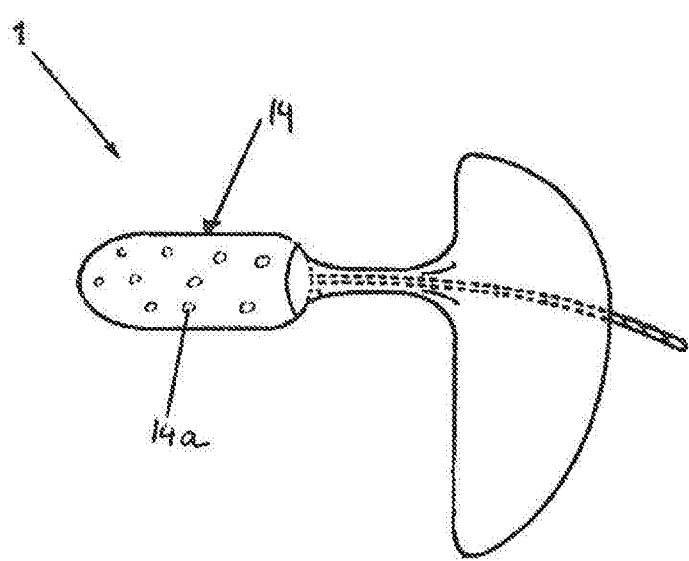
FIG. 8 is a side view of a device according to the present invention comprising a perforated membrane.

In addition, the sheath 4 can expand radially to accommodate the plug 2. More specifically, pulling the cord 9 causes the plug 2 to invert the sheath 4. The inverted sheath 4 expands in a similar way to when accommodating the wearer's finger during insertion and allows the plug 2 to be drawn into the inverted sheath 4, as shown in FIG. 6. So, with the plug 2 accommodated, at least partially, in the inverted sheath 4 and the pad 3 folded over the plug 2, the entire device 1 is enclosed by the liquid impermeable layer of the outward surface 8 of the pad 3 and the sheath 4. This liquid impermeable layer does not come into contact with the cavity opening at any time and is therefore relatively clean. The wearer need only touch the cord 9 and this liquid impermeable layer during removal and disposal of the device 1. So, the device 1 can be hygienically removed and disposed of after use.

Thus, from the above description, it can be seen that the present invention provides a device for the vaginal or rectal delivery of a drug, so that the drug is efficiently and hygienically administered to the target area. The device is user friendly and the drug can be self administered without the need for an experienced practitioner.

The combination of the internally wearable plug, the sheath and the absorbent pad is particularly advantageous in that it provides and all-in-one drug delivery device. The plug can easily and hygienically be inserted in the correct position. The drug can be delivered over a prolonged period of time, without the need for complex formulations or constructions. Any excess fluid and/or medication can be recovered by the absorbent pad.

The invention claimed is:

1. A device for insertion into a human or animal cavity, the device comprising
    an internally wearable medicated plug comprising a pharmaceutically active composition, wherein the medicated plug contains the pharmaceutically active composition, and said pharmaceutically active composition is not in a drug reservoir;
    an externally wearable anchor element; and
    a sheath joining the medicated plug to the anchor element such that a finger can be received in the sheath to assist insertion,
    wherein the medicated plug comprises a heat labile membrane or a liquid labile membrane such that the membrane acts as a protector of the medicated plug when the device is not in use, and wherein the membrane does not comprise the pharmaceutically active composition.

2. The device according to claim 1, wherein the human cavity is a vaginal cavity or a rectal cavity.

3. The device according to claim 1, wherein the composition is a topically active composition.

4. The device according to claim 1, wherein the composition is a systemically active composition.

5. The device according to claim 1, wherein the composition comprises a pharmaceutically active ingredient selected from an antifungal agent, an antibacterial agent, an anti-hemorrhoidal agent and combinations thereof.

6. The device according to claim 1, wherein the composition is releasable in the presence of heat and/or fluid.

7. The device according to claim 1, wherein the composition is selected from the group consisting of a solution, a lotion, a cream, an emulsion, a suspension, an ointment, a paste, a gel, a powder and a foam.

8. The device according to claim 1, wherein the medicated plug comprises an absorbent material.

9. The device according to claim 1, wherein the device further comprises a removable plug cover.

10. The device according to claim 1, wherein the anchor element is an externally wearable absorbent pad.

11. The device according to claim 1, wherein the anchor element comprises an absorbent layer and a liquid impermeable layer.

12. The device according to claim 1, wherein the sheath is flexible.

13. The device according to claim 12, wherein the sheath is expandable only in a radial direction.

14. The device according to claim 1, wherein the sheath comprises an impermeable layer.

15. The device according to claim 14, wherein the impermeable layer is closed where it joins the medicated plug.

16. The device according to claim 1, wherein the sheath comprises an internal impermeable layer and an external absorbent layer.

17. The device according to claim 1, wherein the membrane covers the entire plug.

18. A method for the delivery of a pharmaceutically active composition into a human or animal cavity, the method comprising the step of:
    inserting a finger into the sheath of a device for insertion into a human or animal cavity, the device comprising:
        an internally wearable medicated plug comprising a pharmaceutically active composition, wherein the medicated plug contains the pharmaceutically active composition, and said pharmaceutically active composition is not in a drug reservoir;
        an externally wearable anchor element; and
        a sheath joining the medicated plug to the anchor element such that a finger can be received in the sheath to assist insertion,
        wherein the medicated plug comprises a heat labile membrane or a liquid labile membrane such that the membrane acts as a protector of the medicated plug when the device is not in use, and wherein the membrane does not comprise the pharmaceutically active composition, and
    pushing the medicated plug into the cavity.

19. A method for the treatment of a vaginal or rectal condition, the method comprising the step of:
    inserting a finger into the sheath of a device for insertion into a human or animal cavity, the device comprising:
        an internally wearable medicated plug comprising a pharmaceutically active composition, wherein the medicated plug contains the pharmaceutically active composition, and said pharmaceutically active composition is not in a drug reservoir;
        an externally wearable anchor element; and
        a sheath joining the medicated plug to the anchor element such that a finger can be received in the sheath to assist insertion,
        wherein the medicated plug comprises a heat labile membrane or a liquid labile membrane such that the membrane acts as a protector of the medicated plug when the device is not in use, and wherein the membrane does not comprise the pharmaceutically active composition, and
    pushing the medicated plug into a vaginal cavity or rectal cavity.

* * * * *